(12) United States Patent
Florent et al.

(10) Patent No.: US 9,042,628 B2
(45) Date of Patent: *May 26, 2015

(54) 3D-ORIGINATED CARDIAC ROADMAPPING

(75) Inventors: Raoul Florent, Eindhoven (NL);
Vincent Auvray, Eindhoven (NL);
Michael Grass, Eindhoven (NL); Dirk Schaefer, Eindhoven (NL); Gert Schoonenberg, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 113 days.

This patent is subject to a terminal disclaimer.

(21) Appl. No.: 13/810,292

(22) PCT Filed: Jul. 15, 2011

(86) PCT No.: PCT/IB2011/053169
§ 371 (c)(1),
(2), (4) Date: Jan. 15, 2013

(87) PCT Pub. No.: WO2012/011036
PCT Pub. Date: Jan. 26, 2012

(65) Prior Publication Data
US 2013/0116551 A1 May 9, 2013

(30) Foreign Application Priority Data
Jul. 19, 2010 (EP) .................................... 10305793

(51) Int. Cl.
*G06K 9/00* (2006.01)
*A61B 6/02* (2006.01)
(Continued)

(52) U.S. Cl.
CPC . *A61B 6/022* (2013.01); *A61B 6/12* (2013.01);
*A61B 6/4441* (2013.01); *A61B 6/463* (2013.01);
(Continued)

(58) Field of Classification Search
None
See application file for complete search history.

(56) References Cited

U.S. PATENT DOCUMENTS 4,878,115 A 10/1989 Elion
5,274,551 A 12/1993 Corby, Jr.
(Continued)

FOREIGN PATENT DOCUMENTS

WO WO2006103644 5/2006
WO WO2008104921 4/2008

OTHER PUBLICATIONS

Langs et al, "Building and Registering Parameterized 3D Models of Vessel Trees for Visualization During Intervention", IEEE Compter Society, Proceedings of the 17th International Conference on Pattern Recognition, 2004, pp. 1-4.
(Continued)

*Primary Examiner* — Bhavesh Mehta
*Assistant Examiner* — Feng Niu

(57) ABSTRACT

A 3D-originated cardiac roadmapping device and method include providing 3D+t image data of a vascular structure of an object; acquiring 2D image data of the object that includes the vascular structure, where the 2D image data includes at least one 2D image. The method further includes projecting the vascular structure, thereby generating mask images based on the 3D+t image data; and registering the at least one 2D image with one of the mask images. The registration includes finding the maximum of a similarity factor between the mask images and the at least one 2D image. The method further includes generating a combination of the at least one 2D image and a projection of the vascular structure based on the 3D+t image data according to the registration; and displaying the combination as a guiding vessel tree projection.

18 Claims, 13 Drawing Sheets

(51) Int. Cl.
*A61B 6/12* (2006.01)
*A61B 6/00* (2006.01)
A61B 19/00 (2006.01)

(52) U.S. Cl.
CPC .............. *A61B 6/487* (2013.01); *A61B 6/504* (2013.01); *A61B 6/5223* (2013.01); *A61B 6/5235* (2013.01); A61B 2019/5289 (2013.01); A61B 2019/5295 (2013.01)

(56) References Cited

U.S. PATENT DOCUMENTS

| | | | |
|---|---|---|---|
| 8,244,064 B2* | 8/2012 | Boese et al. | 382/284 |
| 2003/0181809 A1 | 9/2003 | Hall et al. | |
| 2005/0245807 A1* | 11/2005 | Boese et al. | 600/407 |
| 2006/0036167 A1 | 2/2006 | Shina | |
| 2007/0167721 A1* | 7/2007 | Pfister et al. | 600/407 |
| 2008/0009698 A1 | 1/2008 | Boese et al. | |
| 2008/0175455 A1 | 7/2008 | John et al. | |
| 2008/0205722 A1 | 8/2008 | Schaefer et al. | |
| 2008/0247621 A1* | 10/2008 | Zarkh et al. | 382/130 |
| 2008/0275467 A1 | 11/2008 | Liao et al. | |
| 2009/0005668 A1* | 1/2009 | West et al. | 600/407 |
| 2009/0148009 A1 | 6/2009 | Mielekamp et al. | |
| 2010/0049038 A1 | 2/2010 | Florent et al. | |
| 2010/0145193 A1* | 6/2010 | Florent et al. | 600/427 |
| 2013/0322724 A1* | 12/2013 | Florent et al. | 382/132 |

OTHER PUBLICATIONS

Ostermeier et al, "2D Coronary Roadmap Overlaid on 2D Fluoroscopic Image", Siemens AG, 2010, pp. 1-6.
Saybasili et al, "Interventional MRI Using Multiple 3D Angiography Roadmaps With Real-Time Imaging", Journal of Magnetic Resonance Imaging, Vol. 31, Issue 4, pp. 1-10.
Soderman et al, "3D Roadmap in Neuroangiography: Technique and Clinical Interest", Neuroradiology, Vol. 47, 2005, pp. 735-740.
Bredno et al, "Algorithmic Solutions for Live Device-To-Vessel Match", Proceedings of SPIE, Medical Imaging, vol. 5370, 2004, pp. 1486-1497.
Hansis et al, "Four-Dimensional Cardiac Reconstruction From Rotational X-Ray Sequences—First Results for 4D Coronary Angiography", Proceedings for SPIE, vol. 7258, Physics of Medical Imaging, 2009, pp. 1-11.
Turski et al, "Digital Subtration Angiography 'Road Map'", AJR, vol. 139, 1982, pp. 1233-1234.

* cited by examiner

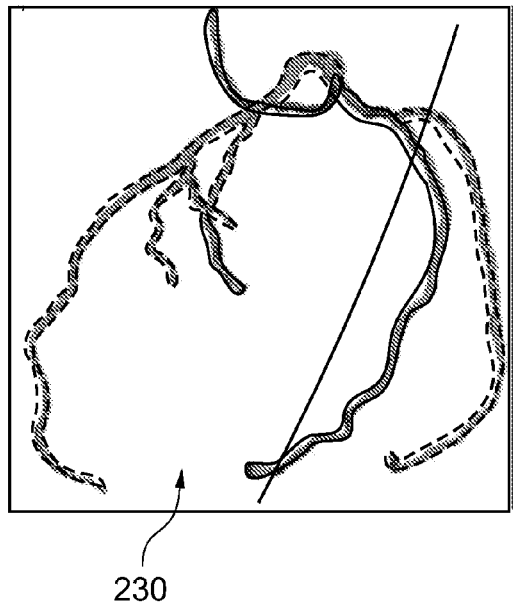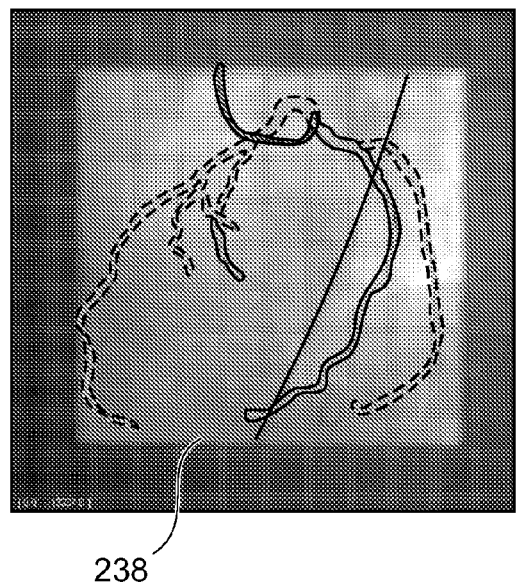
FIG. 18      FIG. 19
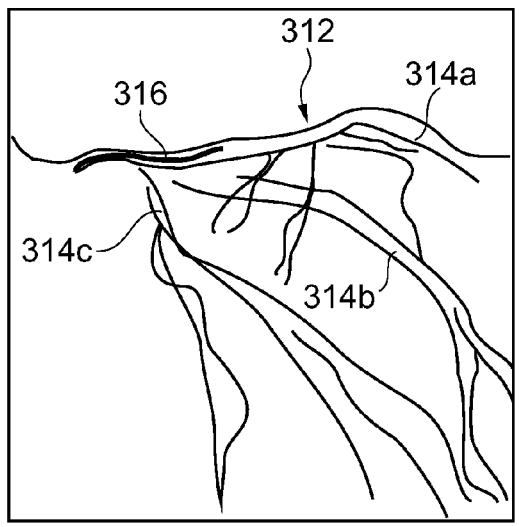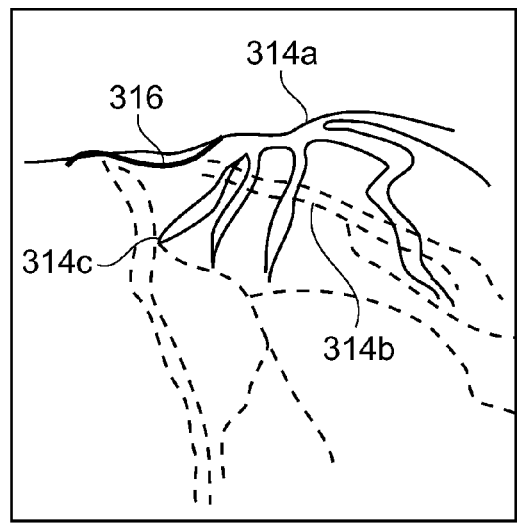
FIG. 20

US 9,042,628 B2

3D-ORIGINATED CARDIAC ROADMAPPING

FIELD OF THE INVENTION

The present invention relates to a device and a method for 3D-originated cardiac roadmapping as well as to a medical imaging system for examination of an object of interest, a computer program element, and a computer readable medium.

BACKGROUND OF THE INVENTION

Navigation systems are known to provide navigating information, for example to a cardiologist, a physician or other clinical staff for example, or to provide the user with information about an object of interest, for example a patient. Such navigation information is in particular needed during catheter interventional procedures, such as PTCA (Percutaneous Transluminal Coronary Angioplasty), for example to treat cardiac stenoses. In WO 2008/104921, cardiac roadmapping is performed on the basis of at least one of a global correlation determination of a first image sequence of the object of interest and a second image sequence of the object of interest and a correlation determination of a first image of the object of interest and a second image of the object of interest on the basis of an identification of a first object and a second object and a first image and a second image. A registration of images relating to an angiogram data set and images relating to a lifetime data set is performed without an additional pairing or image selection step. However, using 2D image data for cardiac roadmapping leads to inaccuracy and confusions.

SUMMARY OF THE INVENTION

Thus, there may be a need to improve the accuracy of the information provided to the user as navigation information, without any additional burden to the patient such as additional X-ray dose.

In the present invention, this is solved by the subject-matter of the independent claims, wherein further embodiments are incorporated in the dependent claims.

It should be noted that the following described aspects of the invention apply also for the device for three-dimensional (3D) originated cardiac roadmapping, the medical imaging system for examination of an object of interest, the method for 3D-originated cardiac roadmapping for examination of an object of interest, the computer program element, and the computer readable medium.

According to an exemplary embodiment of the invention, a method for three-dimensional originated cardiac roadmapping for examination of an object of interest comprises the following steps:
  a) providing 3D+t image data of a vascular structure of an object;
  b) acquiring two-dimensional image data of the object, which object comprises the vascular structure, the 2D image data comprising at least one 2D image;
  c) projecting the vascular structure, thereby generating a plurality of mask images on the basis of a 3D+t image data;
  d) registering the at least one 2D image with one of the plurality of the mask images, wherein the registration comprises finding the maximum of a similarity factor between the mask images and the at least one 2D image;
  e) generating a combination of the at least one 2D image and a projection of the vascular structure on the basis of the 3D+t image data according to the registration; and
  f) displaying the combination as a guiding vessel tree projection.

The term "3D+t image data" relates to 3D image data with time information data, i.e. with a reference over time.

According to a further exemplary embodiment, the 3D+t image data represents a volume comprising at least a part of the vascular structure, which vascular structure comprises a tree-like structure with a plurality of sub-trees. Before step c), the volume is divided into a plurality of sub-volumes, each sub-volume containing a separate sub-tree; in step c), mask images are generated for at least one of the plurality of sub-volumes.

According to one aspect of the invention, the mask images are generated for all sub-volumes, and in step d), the mask images of all sub-volumes are used for the registration.

According to a further exemplary embodiment, before step c), at least one sub-volume is selected, and in step c), the mask images are generated for the selected at least one sub-volume, and in step d), only the mask images of the selected sub-volumes are used for the registration.

According to a further exemplary embodiment of the invention, the volume, which is represented by the 3D+t image data and which comprises at least a part of the vascular structure, comprises a tree-like structure. A plurality of sub-trees and branches are determined and the sub-tree is determined in which an element is positioned. Based on the determined sub-tree, a portion of the vascular structure is selected and visualized in the projection for the combination in step e).

According to a further exemplary embodiment of the invention, branch portions are pruned off and the vascular structure is displayed with a selected portion only.

According to another aspect, the non-selected branch portions are attenuated in relation to their distance to the position of the element, wherein the distance relates to the respective vessel path.

According to a further exemplary embodiment of the invention, a device for 3D-originated cardiac roadmapping is provided, comprising a processing unit, an interface unit, and a display.

The interface unit is adapted to provide 3D+t image data of a vascular structure of an object. The interface unit is further adapted to provide 2D image data of the object, which object comprises the vascular structure, the 2D image data comprising at least one 2D image.

The processing unit is adapted to project the vascular structure, thereby generating a plurality of mask images on the basis of the 3D+t image data, to register the at least one 2D image with one of the plurality of mask images, wherein the registration comprises finding the maximum of a similarity factor between the mask images and the at least 2D image, and to generate a combination of the at least one 2D image and a projection of the vascular structure on the basis of 3D+t image data according to the registration.

The display is adapted to display the combination as a guiding vessel tree projection.

According to a further exemplary embodiment of the invention, a medical imaging system for examination of an object of interest is provided, comprising a device according to the above mentioned exemplary embodiment and X-ray image acquisition means. The X-ray image acquisition means are adapted to acquire the 2D image data of the object, which object comprises the vascular structure, the 2D image data comprising at least one 2D image.

It can be seen as a gist of the invention to provide improved cardiac roadmapping in form of a topographical roadmapping, since the roadmapping is based on three-dimensional data. The cardiac roadmapping is element- or device-based.

In other words, for the registration procedure, the similarity finding uses an element such as a device present in both types of image data, i.e. 3D+t data and 2D (live) image. Because the three-dimensional data is provided as 3D+t data, the topographical roadmapping is also capable of accounting for cardiac motion in real time.

These and other aspects of the present invention will become apparent from and elucidated with reference to exemplary embodiments described hereinafter.

BRIEF DESCRIPTION OF THE DRAWINGS

Exemplary embodiments of the invention will be described in the following with reference to the following drawings:

FIG. 18 schematically shows a customized vessel tree projection.

FIG. 19 schematically shows a tailored guiding vessel tree projection according to the invention.

FIG. 20 schematically shows another example for a generated guiding vessel tree projection and a tailored guiding vessel tree projection.

DETAILED DESCRIPTION OF EXEMPLARY EMBODIMENTS

Figure 1:
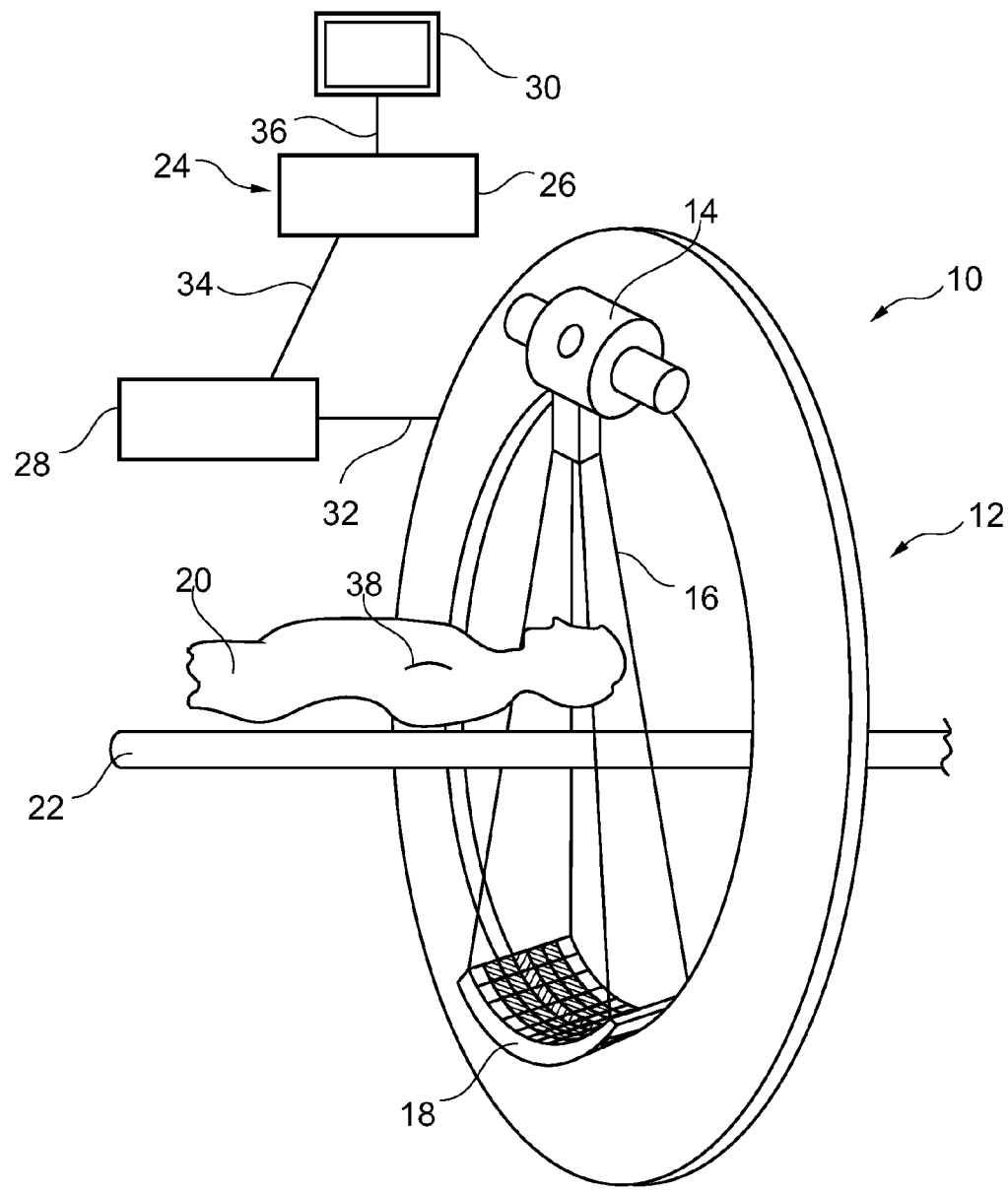
FIG. 1 illustrates an X-ray imaging system with a device for 3D-originated cardiac roadmapping according to an exemplary embodiment of the invention.

FIG. 1 schematically shows a medical imaging system 10, for the use in a catheterization laboratory, for example. The medical imaging system 10 for examination of an object of interest comprises X-ray image acquisition means 12. The X-ray image acquisition means 12 are provided with a source of X-ray radiation 14 to generate X-ray radiation, indicated by an X-ray beam 16. Further, an X-ray image detection module 18 is located opposite the source of X-ray radiation 14 such that, for example, during a radiation procedure, an object, for example a patient 20, can be located between the source of X-ray radiation 14 and the detection module 18. Further, a table 22 is provided to receive the object to be examined.

Further, the medical imaging system 10 comprises a device 24 for 3D-originated cardiac roadmapping. The device 24 comprises a processing unit 26, an interface unit 28, and a display 30.

The interface unit 28 is adapted to provide 3D+t image data of a vascular structure of an object. The interface unit 28 is further adapted to provide 2D image data of the object, which object comprises the vascular structure, the 2D image data comprising at least one 2D image.

The processing unit 26 is adapted to project the vascular structure, thereby generating a plurality of mask images, on the basis of a 3D+t image data. The processing unit 26 is further adapted to register the at least one 2D image with one of the plurality of the mask images, wherein the registration comprises finding the maximum of a similarity factor between the mask images and the at least one 2D image. The processing unit 26 is further adapted to generate a combination of the at least one 2D image and a projection of the vascular structure on the basis of the 3D+t image data according to the registration.

The display 30 is adapted to display the combination as a guiding vessel tree projection.

Further, the acquisition means 12 are adapted to acquire the 2D image data of the object, which object comprises the vascular structure, the 2D image data comprising at least one 2D image. The acquired 2D image data is then provided to the interface unit 28 which is indicated by a first connecting line 32. Then, the interface unit 28 provides the 2D image data to the processing unit which is indicated by a second connecting line 34. The generated combination is provided by the processing unit 26 to the display 30 which is indicated by a third connecting line 36. Of course, the data connections of the above mentioned units and means can also be realized with a wireless connection.

It is noted that the example shown is a so-called CT image acquisition device. Of course, the invention also relates to other types of X-ray image acquisition means, such as a C-type X-ray image acquisition device with a C-arm instead of a circular gentry, as shown in FIG. 1.

The procedure according to the invention is described in more detail below. As mentioned above, the present invention is to be used, for example, by an imaging system for PTCA in catheter laboratories, for example to treat cardiac stenoses.

As a description of the basic interventional procedure, a catheter is inserted into the vascular system at an access site. It is then moved along large vessels to the vascular structure that needs treatment. In order to achieve so-called diagnostic angiograms, contrast agent is injected via the catheter and cathlab X-ray equipment records an angiographic sequence that shows the vessels when filled with contrast agent. The diagnostic angiograms can be used for diagnosis and also for intervention planning. When performing the actual intervention, a guide wire, which is partially or fully radiopaque, is advanced to the vascular structures that need treatment, for example stenoses in coronaries, neurovascular aneurisms, or arterio-venous malformations. The guide wire is then visualized by means of low dose X-ray radiation, so-called fluoroscopic images, such that the interventionalist has some information about the present situation. As one example, the fluoroscopic surveyance allows for the hand-eye coordination of the interventionalist while advancing the guide wire to the target position. When positioned, the guide wire itself serves as a rail to deliver other interventional devices, such as balloons and stents.

In a process referred to as roadmapping, an overlay technique between the angiogram and the live images is provided. For 2D roadmapping, first the artery tree is extracted from angiographies, which lead to a cardiac cycle of artery tree images. Thereby, it is possible to superimpose the artery tree image that covers the live interventional devices to the live fluoroscopic image.

The present invention provides navigation support to reduce the intervention time and also to enhance the positioning accuracy. Further, the aspect of the delivery of contrast agent to the patient is also considered.

According to the invention, 3D+t image data is used, wherein 3D+t techniques deliver state of art vessel maps with a high quality and image information contents.

In contrast to vessel map extraction from 2D angiographies, they do not suffer from confusions due to the background, which leads to finer results. Moreover, more advanced computations, and possibly user interactions, are acceptable, whereas 2D angiography processing needs to respect the interventional work flow, which is implying a close to real time angiography processing and no user interaction.

Furthermore, as an advantage, when 3D+t exams have been carried out anyway, the 3D+t vessel structure, so-to-speak, comes for free. This allows to save some angiographies and thus to reduce dose and contrast agent injection to the patient, if the clinician does not need to perform one angiography under the given acquisition angulation.

As a further advantage, the 3D+t image data use relaxes the constraints imposed to the clinician when he acquires angiographies that are also meant to be used for roadmapping. This also includes the fact that the injection has to last at least one heart cycle. This again saves dose and contrast agent.

As a further advantage, another new possibility lies in the fact that 3D+t based roadmapping also allows C-arm's rotations during the fluoroscopy. For example, if the clinician needs to image the patient from a different angulation during his navigation, because the new perspective allows him to better control his gesture, he would be able to do that smoothly without interrupting the current acquisition.

For a better understanding, it is mentioned that in contrast to the present invention, the angiography based 2D roadmapping requires, in such a case, to stop the fluoroscopy to acquire a new angiography with contrast agent, if no prior such angiography was carried out, and to begin an new fluoroscopy.

As a further advantage for roadmapping coming from 3D+t data, no external signal, for example ECG reading, is required.

According to a further aspect of the invention, the present invention proposes to rely on 3D+t vessel structures that were computed before the intervention to perform a cardiac roadmapping. The 3D+t vessel structure, projected under the fluoroscopy acquisition angulation and animated with a heart motion, is superimposed real time to the live fluoroscopy. This makes the vessels visible to the clinician who, for example, is navigating in them. To perform the superimposition, the invention relies on an element inside the vessels, such as an interventional device. Basically, it makes sure that these devices lie under the re-projected vessels, as they are supposed to be.

Figure 2:
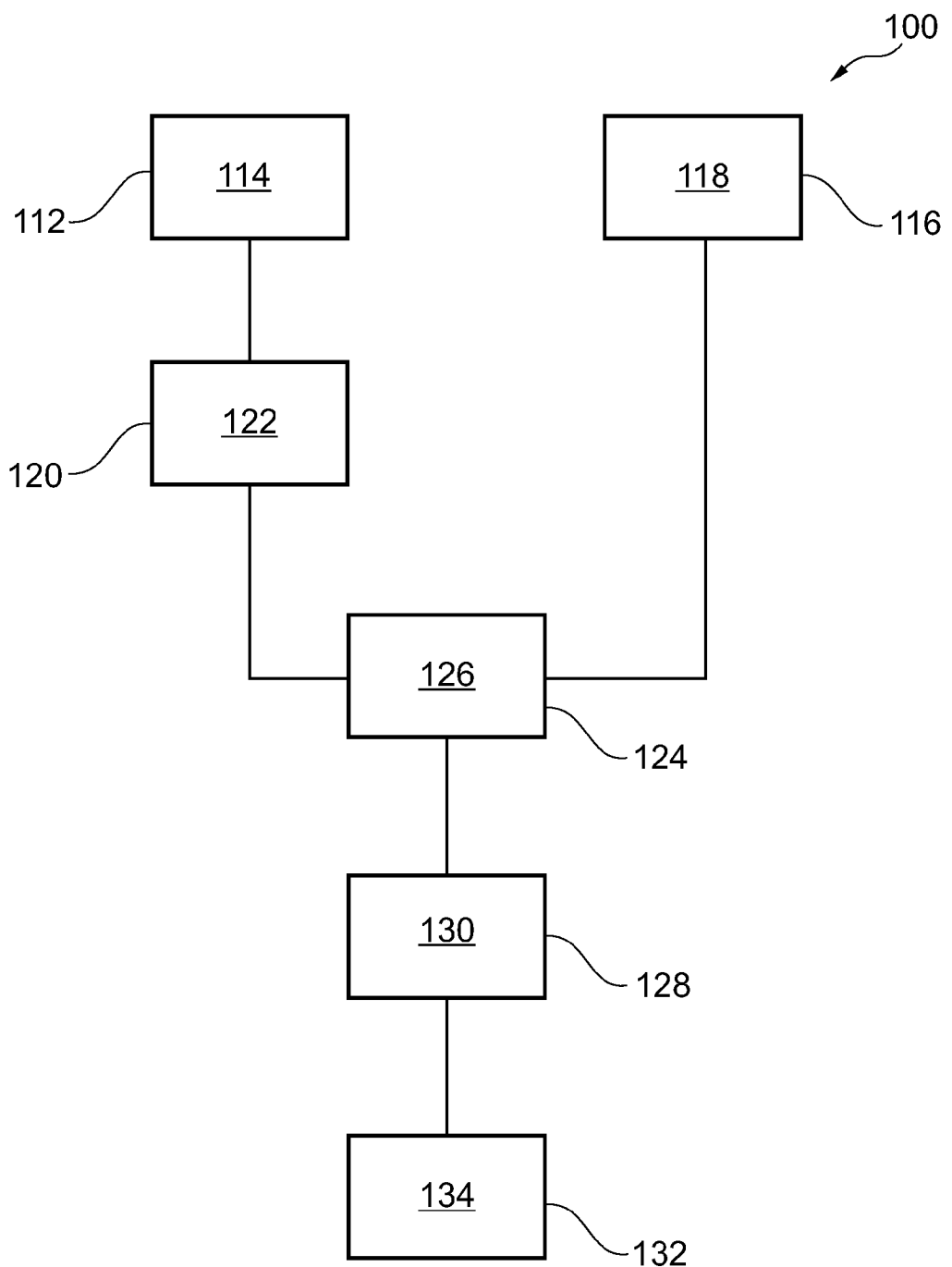
FIG. 2 schematically illustrates the basic method steps of an exemplary embodiment of the invention.

In FIG. 2, an exemplary embodiment of a method 100 for 3D-originated cardiac roadmapping for examination of an object of interest is schematically described. First, in a providing step 112, 3D+t image data 114 of a vascular structure of an object is provided. Further, in an acquisition step 116, 2D image data 118 of the object is acquired, which object comprises the vascular structure, the 2D image data comprising at least one 2D image. In a further projecting step 120, the vascular structure is projected, thereby generating a plurality of mask images 122 on the basis of the 3D+t image data 114.

This projecting step 120 can be performed before the acquisition step 116, for example before the actual intervention.

In a registering step 124, the at least one 2D image is registered with one of the plurality of the mask images, wherein the registration comprises finding 126 the maximum of a similarity factor between the mask images and the at least one 2D image 118.

In a generating step 128, a combination 130 of the at least one 2D image and a projection of a vascular structure on the basis of the 3D+t image data 114, according to the registration 124, is generated.

Further, in a display step 132, the combination 130 is displayed as a guiding vessel tree projection 134.

According to a further aspect of the invention, the 3D+t image data 114 relates to data comprising at least one time-related sequence of 3D image data.

For example, the 3D+t image data is a reconstruction which is reconstructed from a previously acquired sequence of 3D+t image data of the object.

According to a further exemplary embodiment, not shown, the mask images are digitally reconstructed radiography images derived from the 3D+t image data.

According to a further aspect of the invention, the vascular structure is extracted from at least one angiographic sequence. For example, the angiographic sequence is acquired in at least one angular movement.

According to another exemplary embodiment, the 3D+t image data is generated from a set of 2D projections (not shown).

According to a further aspect of the invention, the 3D+t image data is a 3D vessel tree achieved by a volume reconstruction based on the set of 2D projections, and a vessel extraction from the reconstructed volume.

As a further example, the 3D+t image data is provided by pre- or intra-interventional CT examination or C-arm rotation X-ray acquisition.

For example, the 2D image is a live X-ray fluoroscopy image of the vascular structure.

Figure 3:
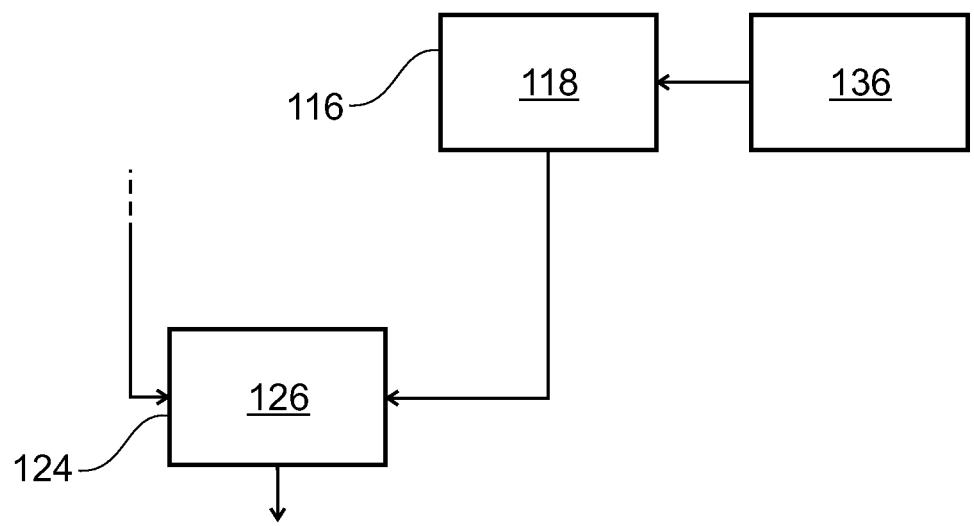
FIGS. 3 to 12 show further exemplary embodiments of method steps according to the invention.

With respect to the acquisition step 116, according to a further exemplary embodiment, shown in FIG. 3, the 2D image data 118 is acquired with acquisition parameters 136, for example along a viewing direction.

According to a further aspect of the invention, in the 2D image data 118 of the object, the vascular structure is less visible than in the 3D+t image data 114. Preferably, the vascular structure is not visible in the 2D image data 118.

According to a further exemplary embodiment, the 2D image data 118 comprises a sequence of 2D images (not shown).

As a further example, the 2D images are device maps computed on a sequence of 2D images. In such device maps, a device is shown by pixels enhanced in one or several computational steps manipulating the raw 2D image data.

With respect to the projecting step 120, the mask images are 2D mask images.

According to an exemplary embodiment of the invention, the mask images 122 are 2D images corresponding to 2D image data acquired with acquisition parameters, for example along a viewing direction. In other words, the 2D mask images are computed according to the projection geometry data during the acquisition of the 2D image data 118. Of course, in such a case, the projecting step 120 has to be performed after the acquisition step 116.

According to a further embodiment, in the projecting step 120, a plurality of mask images is generated on the basis of at least one of the acquisition parameters.

For example, the 2D mask images are computed from the 3D+t image data.

With respect to the registering step 124, this step is also referred to as comprising a similarity measurement.

Figure 4:
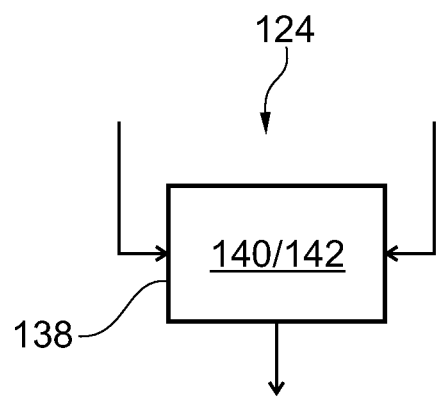

According to a further exemplary embodiment, shown in FIG. 4, the registration step 124 comprises the simultaneous finding 138 of the image geometry 140 with a maximum similarity of the transform/translation 142 with a maximum similarity. For example, a weighting or scoring is performed in a parallel manner for each parameter.

Figure 5:
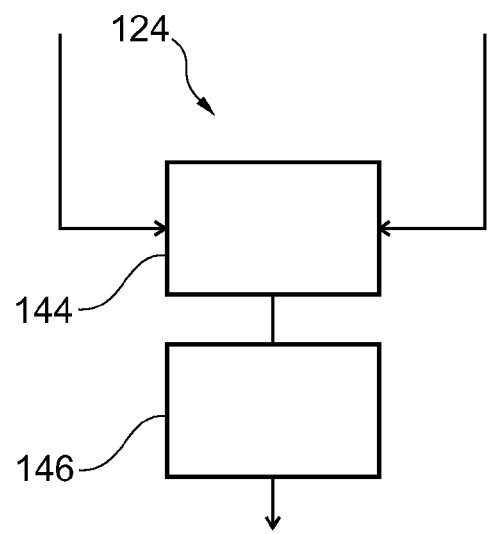

According to another exemplary embodiment, shown in FIG. 5, the registration step 124 comprises a first sub-step of finding 144 the image geometry with a maximum similarity and the second sub-step 146 of finding 146 the transform/translation with a maximum similarity.

For example, the first sub-step 144 comprises selecting mask images according to a certain time reference, for example according to a determination cardiac phase.

Further, as an example, the projection of the vascular structure for the combination comprises alignment factors derived from the registration step 124.

The alignment factors, for example, comprise table panning correction, pixel shift, breathing correction and cardiac motion correction.

With respect to the generating step 128, a projection of the vascular structure on the basis of the 3D+t image data is generated.

Figure 6:
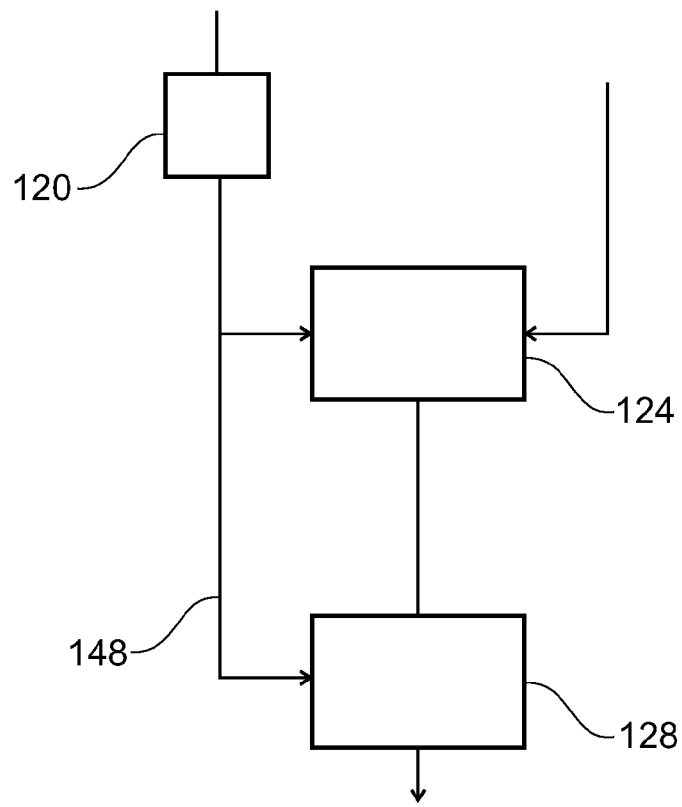

According to another exemplary embodiment, shown in FIG. 6, in the registration step 128, a mask image or a combination of mask images is provided indicated by arrow 148 as the projection. The mask images or a combination of mask images is derived from the projecting step 120.

Figure 7:
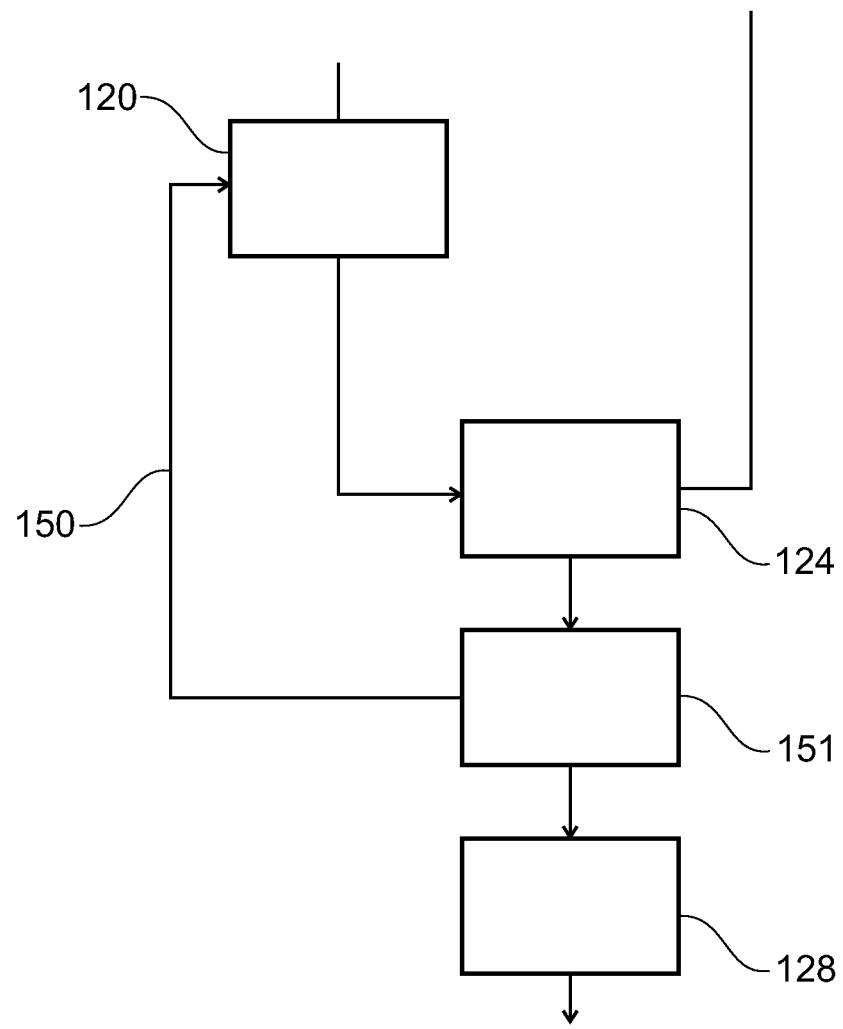

According to a further exemplary embodiment, shown in FIG. 7, the projecting step 120 and the registering step 124 are repeated one or more times as iteration steps before performing the generating step 128. The repetition is indicated with a loop-like arrow 150.

It should be noted that the providing step 112 is also referred to as step a), the acquisition step 116 as step b), the projecting step 120 as step c), the registering step 124 as step d), the generating step 128 as step e) and the displaying step 132 as step f).

In FIG. 7, a decision box 151 is added following the registration step 124. Of course, such decision box can be omitted, for example if the repetition indicated by arrow 150 is repeated for a predetermined number of times. However, the decision box 151 provides the possibility to base the decision, whether a repetition is performed or not, on the result of the registration step 124. If such result is according to the desired needs and accuracy respectively, the following step 128 is performed.

According to an exemplary embodiment, an element 38 (see FIG. 1) is located inside the vascular structure, for example a stent or guide wire, which element is visible in the 2D image data and the registration is based upon the element.

According to a further exemplary embodiment (not shown), the 3D+t image data comprises a phase reference signal, wherein the plurality of mask images each comprises a phase indicator, and wherein the registration of the 2D image from the plurality of the 2D mask images only images with a corresponding phase reference or selected.

For example, for the registration of the 2D image, image pixels with a first predetermined value are matched with image pixels or voxels with a predetermined second value.

Further, it should be noted that according to an exemplary embodiment, the registration step comprises temporal and spatial constraints. For example, the temporal and spatial constraints are based upon previously performed registrations.

According to further exemplary embodiment, a possible moving path of the element inside the 3D+t model of the vascular structure is determined.

Figure 8:
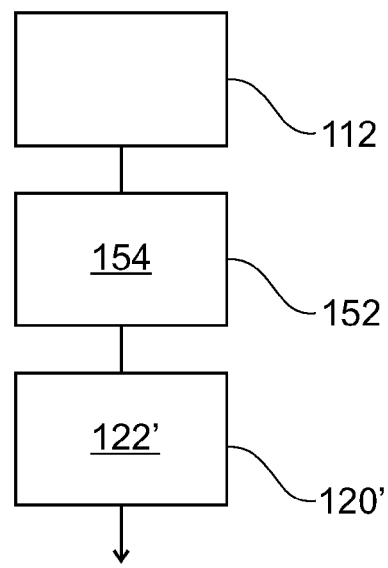

According to another exemplary embodiment shown in FIG. 8, the 3D+t image data represents a volume comprising at least a part of a vascular structure 202, which vascular structure comprises a tree-like structure (for example, see FIG. 14), indicated with reference numeral 212, with a plurality of sub-trees 214. Before the projecting step 120, the volume is divided 152 into a plurality of sub-volumes 154, each sub-volume containing a separate sub-tree 214 and wherein in step c), mask images 122' are generated 120' for at least one of the plurality of sub-volumes.

According to an exemplary embodiment, in step c), mask images are generated for all sub-volumes, and in step d), mask images of all sub-volumes are used for the registration.

According to another exemplary embodiment, in step d), mask images of a reduced number of sub-volumes are used for the registration.

Figure 9:
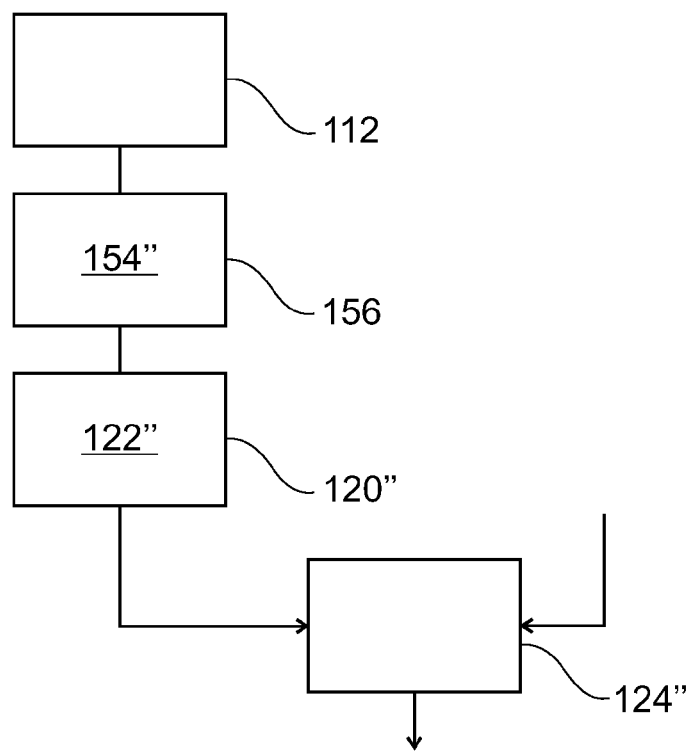

According to further exemplary embodiment, shown in FIG. 9, before the projecting step 120, at least one sub-volume is selected 156 and in step c), i.e. the generation step, mask images 122" are generated 120" for the selected at least one sub-volume. In step d), only mask images of the selected sub-volumes are used for the registration 124".

For example, a branch of interest of the vascular structure is determined and the sub-volume containing the determined branch is selected. As another example, sub-volumes adjacent to the selected sub-volume are also selected.

As a further example, a weighting factor can be applied to the adjacent sub-volumes, for example only part volumes of the adjacent sub-volumes along the adjacent border region are selected.

According to a further exemplary embodiment, not further shown, the element is identified and localized in the 2D image. As an example, the element is an interventional device. As a further example, the element comprises at least two features immovably attached to the object, for example to the patient's body, for example an immovably attached implant. As a further example, the element comprises classification structures of a heart vessel tree that can be detected in the 2D image.

Figure 10A:
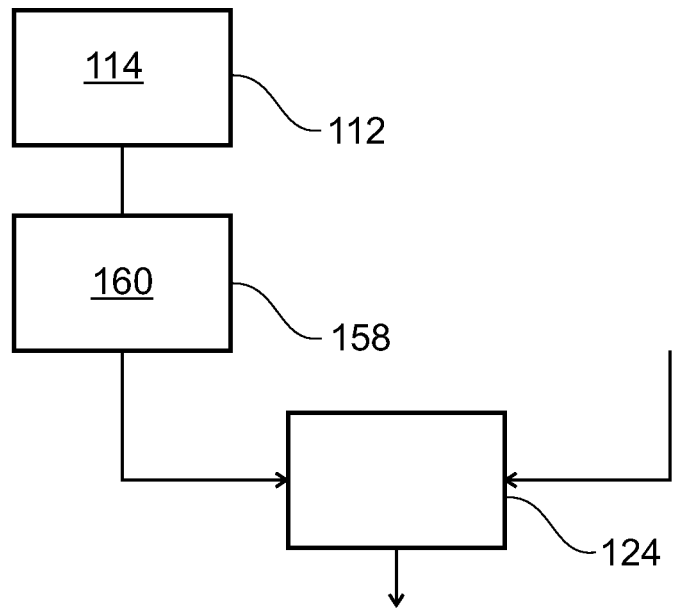

According to another exemplary embodiment, shown in FIG. 10a, the vascular structure with its vessel volumes is determined 158 by vessel segmentation 160 on the basis of the 3D+t image data 114 and the 2D image is registered such that an element in the 2D image is positioned inside a vessel of the vascular structure.

Figure 10B:
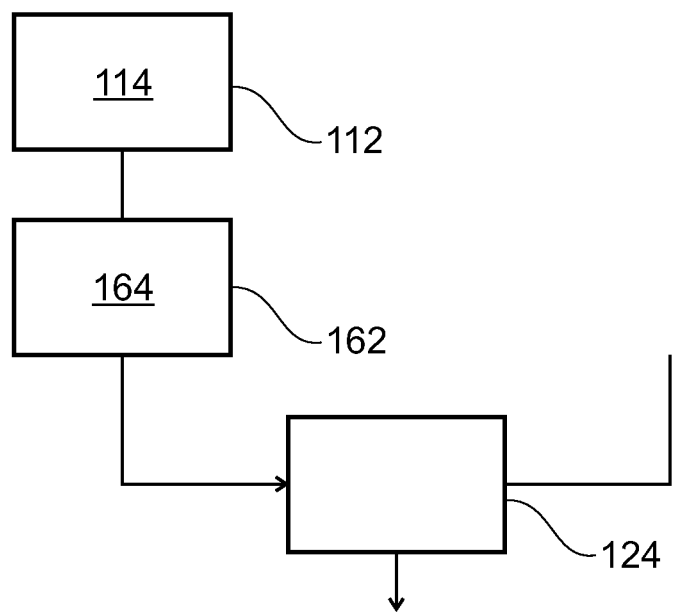

According to a further exemplary embodiment, the vascular structure with its vessel volumes is determined by generating 162 a model 164 (see FIG. 10b) from the 3D+t image data 114. The 2D image is registered such that an element in the 2D image is positioned inside a vessel of the vascular structure.

According to a further aspect, the element is detected and a model of the element is generated and displayed overlaid to the 2D image.

As a further example, the 2D image comprises at least two elements and the at least two elements are located inside the vascular structure.

Figure 11:
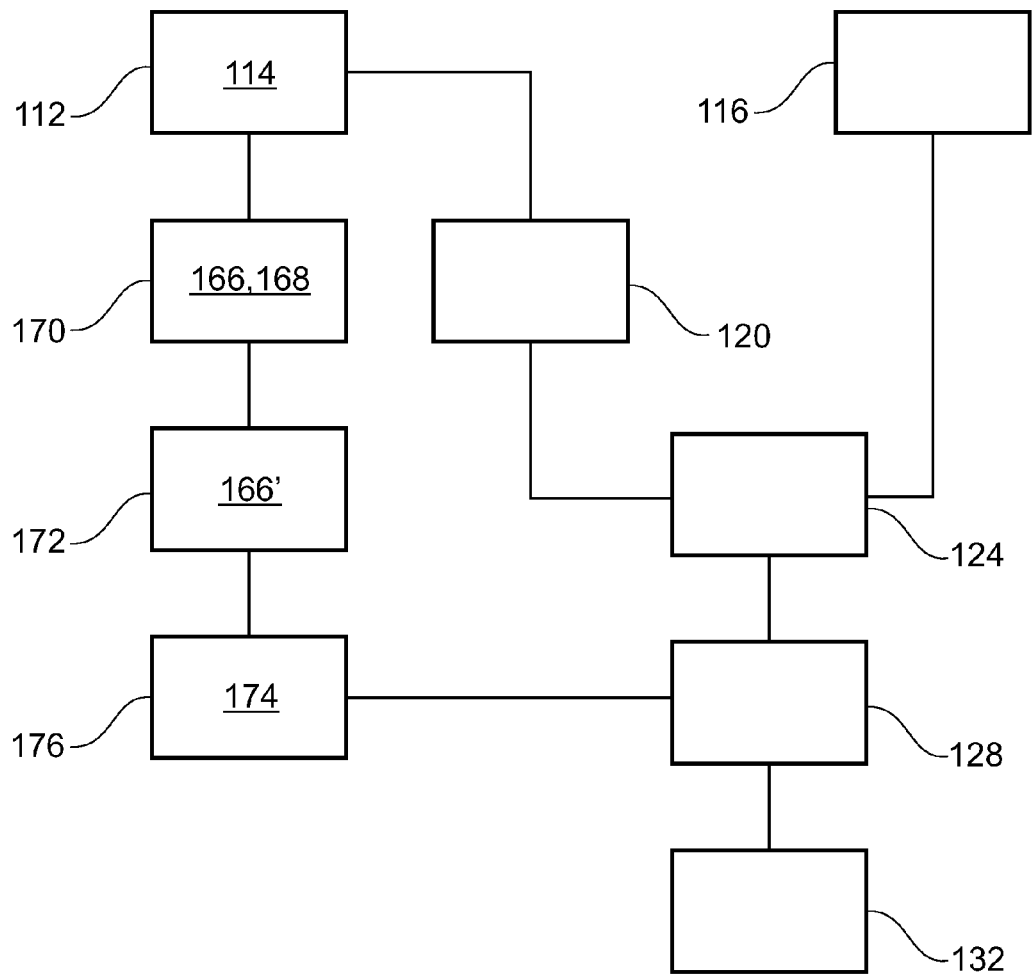
Figures 13, 14, 15:
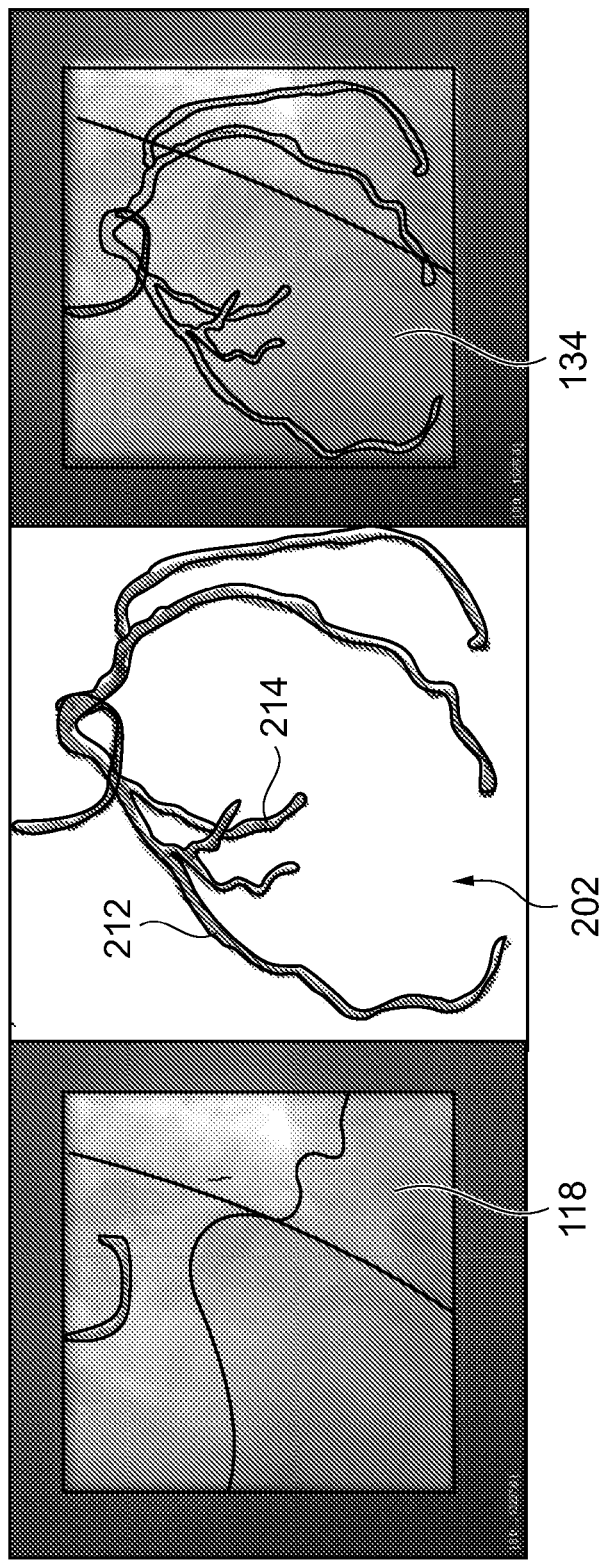
FIG. 13 schematically shows an acquired 2D image.
FIG. 14 schematically shows a projection of a vascular structure.
FIG. 15 schematically shows a generated guiding vessel tree projection according to the invention.

According to a further exemplary embodiment of the invention, shown in FIG. 11, the volume which is represented by the 3D+t image data 114 and which comprises at least a part of the vascular structure, comprises a tree-like structure, such as mentioned with reference to FIG. 14, and a plurality of sub-trees 166 and branches 168 are determined 170. A sub-tree 166' is determined 172 in which an element is positioned. Based on the determined sub-tree 166', a portion 174 of the vascular structure is selected and visualized 176 in the projection for the combination in step e), i.e. for the combination 130 in the generating step 128.

According to a further exemplary embodiment, the non-selected branch portions are pruned off and the vascular structure is displayed with the selected portion only.

For example, the vessel tree with pruned off branches is a segmented topographical road map.

According to another aspect, in addition, the pruned off branches are shown in a valuated map, for example the pruned branches are shown in a semi-opaque manner.

According to a further aspect, the pruned branches are shown in a different colour.

According to a further aspect, the non-selected vascular structure is attenuated in relation to the distance to the element. In other words, the vessel structure is fading the more, the greater the distance of the vessel path to the element. The term "distance" relates to the connecting path inside the vessel tree structure.

According to a further aspect of the invention, temporal information is recorded and element motion is determined on behalf of the temporal information. Based on the previously determined position inside the vessel volume, the actual vessel in which the element is positioned is identified.

For example, the identified vessel location is verified by a re-registration step.

Figure 12:
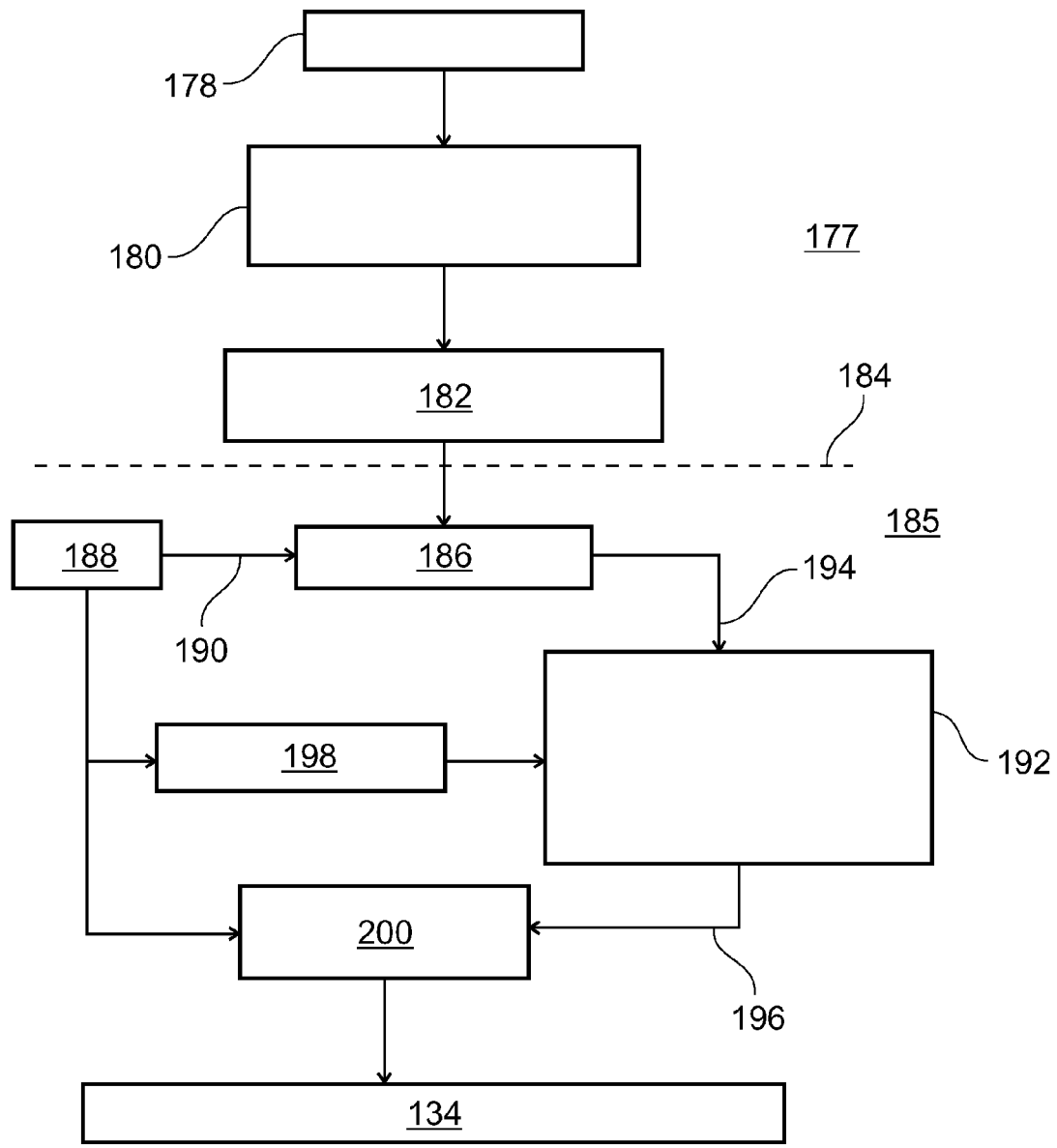

Another exemplary embodiment will now be described with reference to FIG. 12. In a first stage 177, a rotational sequence is acquired 178. The rotational sequence is processed and the 3D+t vessel map is computed 180. For example, the rotational acquisition 178 can be a single angular movement or a movement around more than one angle, for example as dual axis rotation trajectories. The 3D+t vessel map can be directly extracted from the set of 2D projections, or it can be performed in two steps, namely volume reconstruction and vessel extraction. As a result 182, the 3D+t vessel structure with referential in the cathlab, i.e. with known physical coordinates in the cathlab, is provided. Of course, the above mentioned steps can be provided in a pre-interventional phase, which is indicated by a separating line 184, shown in a dotted manner.

In a second stage 185, shown below the separation line 184, from the angulation acquisition the extracted vessel structure can be projected 186 from the proper perspective. Therefore, from a 2D acquisition in fluoroscopy 188, an angulation factor is provided which is indicated by a first arrow 190 entering the projecting box 186. From the projection box 186, a projected vessel structure is provided to a further computational step 192, which providing of the projected vessel structure is indicated by a second arrow 194. The series of 2D vessel structures thus provided are corrected in the computational step 192 for potential geometric transformations (zoom etc.) resulting from table panning, SID change etc.

Thus, projected vessel structure at the proper time and with a proper spatial shift are provided, which is indicated by a third arrow 196, leaving the computational step box 192.

Further, the sequence of 2D structures provided by fluoroscopy 182 is confronted with a device map, computed on the fluoroscopic images. Under the constraints that as many devices must be covered by the overlay and that the temporal and spatial changes must be as smooth as possible from a fluoroscopic image to the next, the best 2D structure is extracted from the projected sequence and it is moved with its best spatial shift.

For a device extraction 198, images from the fluoroscopy 188 are provided. The device extraction can either be performed hard or soft. The result is entering the computational box 192. Further, fluoroscopy images 188 are also provided to an overlay step 200, in which the selected and shifted 2D structure is overlaid to the live fluoroscopic image, together with a volume rendering, i.e. a 3D rendering. As a result, the projected vessel structure over the live fluoroscopy sequence is provided as the guiding vessel tree projection 134.

According to another aspect, the warping is not limited to a translation; any geometric transformation is possible.

It must be noted that the invention is not limited to cardiac exams. In particular, exams that need breathing compensation can take advantage from the present invention.

According to a further aspect, it is also possible to present the clinician, along with the topographical roadmapping, a projection of the current vessel structure from another perspective, so that he or she can apprehend the vessels geometry more easily.

According to a further aspect, as soon as the device and the 3D tree have been registered for the first time, the path towards a target lesion selected prior in the 3D+t data is simulated by visualizing the forward projected 3D+t data set and overlaid in a virtual device as it is moving towards the lesion.

In FIG. 13, an example for the 2D image 118 acquired under 2D fluoroscopy is shown. In FIG. 14, a vessel structure 202 is shown derived from 3D+t image data 114.

In FIG. 15, the combination of the 2D image 118 and the projection of the vascular structure 202 shown in FIG. 14 are provided as the guiding vessel tree projection 134.

Figure 16:
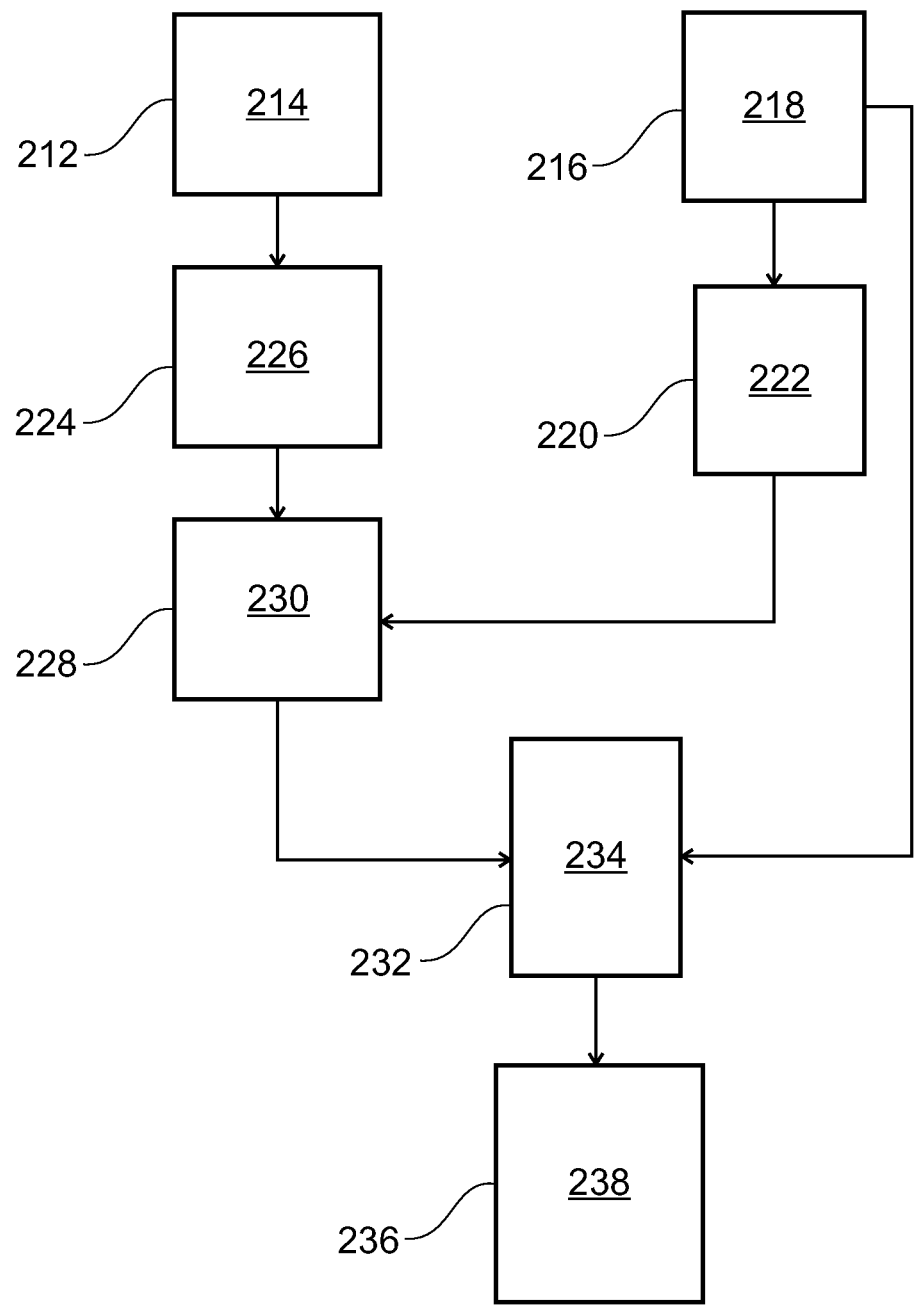
FIGS. 16 and 17 show further exemplary embodiments of method steps according to the invention.

FIG. 16 schematically shows an exemplary embodiment of a method for dynamic vessel road map pruning. In a first step 212, pre-navigation data 214 is provided, for example a 3D vessel tree of the C-arm CT reconstruction. Further, in a providing step 216, navigation data 218 is provided, for example 2D live fluoroscopy images during an intervention. In a next step, following the providing step 216, which is referred to as a analyzing step 220, the navigation data, for example the live images, are constantly analyzed to identify and localize an intervention device 222 or a plurality of interventional devices. For example, this can be achieved by applying standard tracking techniques. For example, typical targeted devices are endo-prosthesis such as a stent, flow diverter, coil etc., or the tools used to percutaneously localize, steer, position, deploy or implant those prosthesis such as wire, catheter, marker, balloon, etc.

In a further computational step 224, a vessel representation 226 is computed from the pre-navigation data. For instance, this might be a grey level transformation of the pre-navigation pixels or voxels, for instance a lookup table on the angiogram pixel or voxel values. It might also be a binary mask computed from such angiogram images, for instance through adapted filtering and thresholding. When emanating from three-dimensional data, the vessel representation might be a full segmentation of modelling of the vasculature, i.e. the vascular structure, present in the 3D pre-navigation data.

The output from the computational step 224 is then provided to a following pruning step 228 in which the actual pruning of the vessel representation occurs. It first consists in determining in which vessel branch or vessel sub-tree the intervention devices are currently situated. Of course, at a given instant, there might be a certain degree of incertitude or ambiguity concerning the question which vessel, branches or sub-volume indeed contain the intervention device. However, using the temporal information, from the temporal tracking in the identification or analyzing step 220 and the vessel or device motions which are also provided by the analyzing step 220, it is possible to quickly identify which vessel actually contains the identified device. Once identified, the irrelevant vessels are either removed, for instance when the vessel representation is a segmentation result, or they might be attenuated, in particular if the vessel representation is a valuated map. In the latter case, the vessel representation can also be presented as fading away, as mentioned above, at those pixels where the distance to the intervention devices is substantially large. Thus, a pruned representation 230 is provided by the pruning step 228 (see FIG. 18). Finally, the pruned representation 230 is combined with the live images from the navigation data 218 in an overlay step 232. Thus, a combination 234 is generated. Following, in a displaying step 236, the combination 234 is provided as a pruned guiding vessel tree projection 238 (see FIG. 19).

In another exemplary embodiment of the pruning method, the pre-navigation data 214 is provided to a registration step 240 in which the pre-navigation data 214 is registered with the live images 218 is provided by the providing step 216. As a result of the registration step, which can also be referred to as an optional matching step, registration data 242 is provided to the computational step 224, where the vessel representation 226 is computed.

Figure 17:
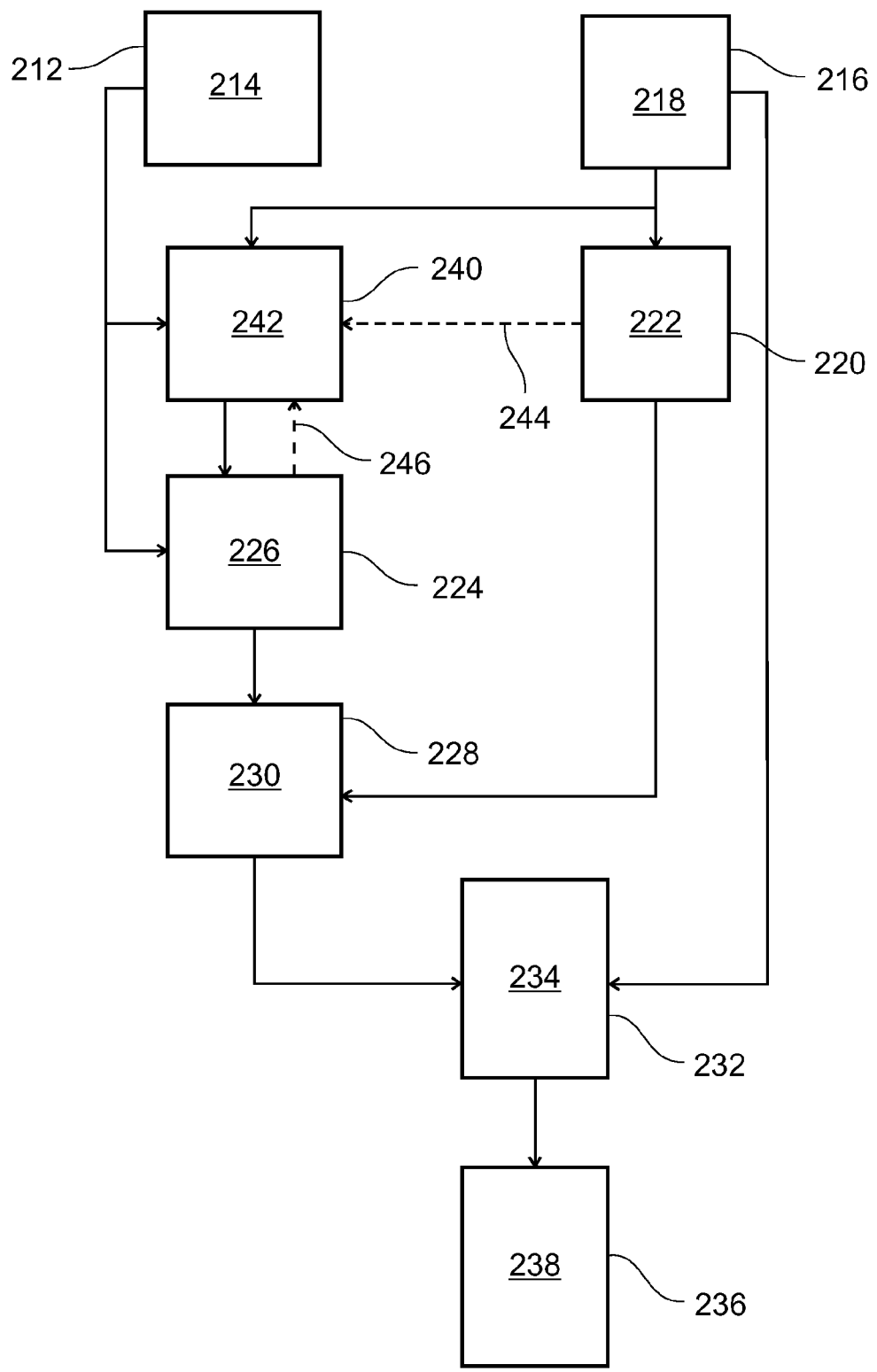

As a further option, also indicated in FIG. 17, the registration step 240 can take advantage of the output of the device tracking module of the analyzing step 220, which is indicated by a dotted arrow 244.

Likewise, the registration step 240 can rely on the generation of the vessel representation and/or its projection along the live viewing direction to perform the matching task. This is indicated by a second dotted arrow 246 coming from the vessel representation step 224 entering the registration step 240.

According to an aspect of the invention, the registration of the vessel representation with live data is responsible for the quality of the image and the image content provided to the user.

In FIG. 20, a pruned guiding vessel tree projection 238 is shown in the right half and a guiding vessel tree projection 134, i.e. a topographical road map without pruning, is shown in the left half. As can be seen, a vessel tree 312 is shown comprising several sub-trees 314, only a few of these are indicated with reference numerals. Further, as the element 38, an interventional device 316 is also visible. The interventional device 316, for example a guide wire of a catheter, is visible in the 2D live images which are used for the combination shown in FIG. 20. The vessel tree information is based on 3D-originated cardiac roadmapping technique as described above. As described with references to FIGS. 16 and 17, and also in the description above, the vessel sub-tree 314a in which the interventional device 316 is located, is shown in a different manner than those in which the interventional device is not located. For instance, the selected sub-tree is displayed with straight lines and the sub-trees, which are determined as not containing the interventional device, i.e. sub-trees 314b and 314c, are pruned off. For example, they can be simply not displayed or, as in the right half of FIG. 20, they can be shown in a dotted line manner, to provide additional information, but which information does distract the user less since it is shown in a different way than the selected sub-tree 314a.

In another exemplary embodiment of the present invention (not shown), a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an update turns an existing program into a program that uses the invention.

Further on, the computer program element might be able to provide all necessary steps to fulfil the procedure of an exemplary embodiment of the method as described above.

According to a further exemplary embodiment of the present invention (not shown), a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage.

The invention claimed is:

1. A device for 3D-originated cardiac roadmapping, comprising:
    a processor configured to receive 3D+t image data of a vascular structure of an object; and to receive 2D image data of the object, the 2D image data comprising at least one 2D image; and
    a display;
    wherein the processor is further configured to
        project the vascular structure, thereby generating a plurality of mask images based on the 3D+t image data;
        perform a registration of the at least one 2D image with one of the plurality of the mask images by finding a maximum of a similarity factor between the plurality of mask images and the at least one 2D image; and
        generate, according to the registration, a combination of the at least one 2D image and a projection of the vascular structure based on the 3D+t image data;

wherein the display is configured to display the combination as a guiding vessel tree projection,
wherein an element is located inside a vessel of the vascular structure,
wherein the element is visible in the 2D image data, and
wherein the display is further configured to display the combination as the guiding vessel tree projection having sub-branches, wherein sub-branches of the sub-branches that do not include the element are attenuated based on a distance from the element for greater fading as the distance increases.

2. The device of claim 1, wherein the processor determines the vessel that includes the element using temporal information from temporal tracking of the element in the vascular structure.

3. The device of claim 1, wherein the processor is further configured to determine the vessel that includes the element, wherein the registration is based upon the element positioning the element visible in the 2D image data inside the vessel visible in the 3D-t image data.

4. A medical imaging system for examination of an object of interest, comprising:
a device for 3D-originated cardiac roadmapping; and
an X-ray imager;
wherein the X-ray imager is configured to acquire 2D image data of the object,
wherein the device comprises a processor and a display, the processor being configured to
receive 3D+t image data of a vascular structure of the object,
receive the 2D image data of the object, the 2D image data comprising at least one 2D image,
project the vascular structure for generating a plurality of mask images based on the 3D+t image data,
perform a registration of the at least one 2D image with one of the plurality of the mask images by finding a maximum of a similarity factor between the plurality of mask images and the at least one 2D image, and
generate, according to the registration, a combination of the at least one 2D image and a projection of the vascular structure based on the 3D+t image data,
wherein the display is configured to display the combination as a guiding vessel tree projection,
wherein an element is located inside a vessel of the vascular structure,
wherein the element is visible in the 2D image data, and
wherein the display is further configured to display the combination as the guiding vessel tree projection having sub-branches, wherein sub-branches of the sub-branches that do not include the element are attenuated based on a distance from the element for greater fading as the distance increases.

5. The medical imaging system of claim 4, wherein the processor determines the vessel that includes the element using temporal information from temporal tracking of the element in the vascular structure.

6. The medical imaging system of claim 4, wherein the processor is further configured to determine the vessel that includes the element, wherein the registration is based upon the element by positioning the element visible in the 2D image data inside the vessel visible in the 3D+t image data.

7. A method for 3D-originated cardiac roadmapping for examination of an object of interest, the method comprising the acts of:
providing 3D+t image data of a vascular structure of the object;
acquiring 2D image data of the object, wherein the object comprises the vascular structure, the 2D image data comprising at least one 2D image;
projecting the vascular structure, thereby generating a plurality of mask images based on the 3D+t image data;
registering the at least one 2D image with one of the plurality of the mask images by finding a maximum of a similarity factor between the plurality of mask images and the at least one 2D image;
generating, according to the registration, a combination of the at least one 2D image and a projection of the vascular structure based on the 3D+t image data; and
displaying the combination as a guiding vessel tree projection;
wherein an element is located inside the vascular structure and is visible in the 2D image data, and
wherein the displaying act displays the combination as the guiding vessel tree projection having sub-branches, wherein sub-branches of the sub-branches that do not include the element are attenuated based on a distance from the element for greater fading as the distance increases.

8. The method according to claim 7, wherein the 3D+t image data comprises a phase reference signal; wherein the plurality of mask images each comprises a phase indicator; and wherein for the registering act, from the plurality of the mask images only images with a corresponding phase reference are selected.

9. The method according to claim 7, wherein the 3D+t image data represents a volume comprising at least a part of the vascular structure, wherein the vascular structure comprises a tree-like structure with a plurality of sub-trees; and wherein before the projecting act, the volume is divided into a plurality of sub-volumes, each sub-volume containing a separate sub-tree; and wherein projecting act generates mask images for at least one of the plurality of sub-volumes.

10. The method according to claim 7, wherein before the projecting act, at least one sub-volume is selected; and wherein projecting act generates mask images for the selected at least one sub-volume; and wherein the registering act uses only mask images of the selected sub-volumes.

11. The method according to claim 7, wherein the element is identified and localized in the at least one 2D image.

12. The method according to claim 7, further comprising the act of determining the vascular structure with its vessel volumes by vessel segmentation based on the 3D+t image data; and wherein the registering act registers the at least one 2D image such that the element in the 2D image data is positioned inside a vessel of the vascular structure.

13. The method according to claim 7, further comprising the act of determining the vascular structure with its vessel volumes by generating a model from the 3D+t image data; and wherein the registering act registers the at least one 2D image such that the element in the 2D image is positioned inside a vessel of the vascular structure.

14. The method according to claim 7, wherein a volume, which is represented by the 3D+t image data and which comprises at least a part of the vascular structure, comprises a tree-like structure; and the method further comprises the acts of:
determining a plurality of sub-trees and branches; and
determining a sub-tree including the element in the determined sub-tree;
based on the determined sub-tree, selecting a portion of the vascular structure; and visualized
visualizing the selected portion in the projection used for the act of generating the combination.

15. The method according to claim 14, wherein non-selected branch portions are pruned off and wherein the displaying act displays the vascular structure with the selected portion only.

16. The method of claim 7, wherein the processor determines the vessel that includes the element using temporal information from temporal tracking of the element in the vascular structure.

17. The method of claim 7, further comprising the act of determining the vascular structure that includes the element, wherein the registering act is based upon the element by positioning the element visible in the 2D image data inside the vascular structure visible in the 3D+t image data.

18. A non-transitory computer readable medium comprising computer instructions which, when executed by a processor, configure the processor to perform 3D-originated cardiac roadmapping for examination of an object of interest by performing the acts of:

provebounds 3D+t image data of a vascular structure of the object;

acquiring 2D image data of the object, wherein the object comprises the vascular structure, the 2D image data comprising at least one 2D image;

projecting the vascular structure, thereby generating a plurality of mask images based on the 3D+t image data;

registering the at least one 2D image with one of the plurality of the mask images by finding a maximum of a similarity factor between the plurality of mask images and the at least one 2D image;

generating, according to the registration, a combination of the at least one 2D image and a projection of the vascular structure based on the 3D+t image data; and displaying the combination as a guiding vessel tree projection;

wherein an element is located inside the vascular structure and is visible in the 2D image data, and wherein the displaying act displays the combination as the guiding vessel tree projection having sub-branches, wherein sub-branches of the sub-branches that do not include the element are attenuated based on a distance from the element for greater fading as the distance increase.

* * * * *